United States Patent [19]

Berg et al.

[11] Patent Number: 4,801,358

[45] Date of Patent: Jan. 31, 1989

[54] SEPARATION OF ACETIC ACID FROM DIOXANE BY EXTRACTIVE DISTILLATION

[76] Inventors: Lloyd Berg; Rudolph J. Szabados, both of 1314 S. Third Ave., Bozeman, Mont. 59715

[21] Appl. No.: 225,199

[22] Filed: Jul. 28, 1988

[51] Int. Cl.$^4$ .................... B01D 3/40; C07C 53/02; C07D 319/12

[52] U.S. Cl. .................... 203/51; 203/56; 203/60; 203/61; 203/62; 203/63; 203/64; 549/377; 562/608

[58] Field of Search .............. 203/60, 51, 61, 63, 203/62, 56; 549/377; 562/608, 607

[56] References Cited

U.S. PATENT DOCUMENTS

| | | | |
|---|---|---|---|
| 2,441,114 | 5/1948 | Krieble et al. | 549/377 |
| 4,007,095 | 2/1977 | Wolf et al. | 549/377 |
| 4,336,195 | 6/1982 | Renga | 549/377 |

FOREIGN PATENT DOCUMENTS

| | | | |
|---|---|---|---|
| 44-29858 | 12/1969 | Japan | 549/377 |
| 49-54324 | 5/1974 | Japan | 562/608 |
| 55-85584 | 6/1980 | Japan | 549/377 |
| 967471 | 12/1960 | United Kingdom | 203/60 |
| 2172887 | 10/1986 | United Kingdom | 549/377 |

Primary Examiner—Wilbur Bascomb

[57] ABSTRACT

Dioxane cannot be completely removed from dioxane and acetic acid mixtures by distillation because of the presence of the maximum azeotrope. Dioxane can be readily removed from dioxane - acetic acid mixtures by extractive distillation in which the extractive agent is N,N-dimethylacetamide or dimethylformamide, either alone or mixed with certain high boiling organic compounds. Examples of effective agents are N,N-dimethylacetamide; dimethylformamide and heptanoic acid; N,N-dimethylacetamide, heptanoic acid and diethylene glycol diethyl ether.

3 Claims, No Drawings

SEPARATION OF ACETIC ACID FROM DIOXANE BY EXTRACTIVE DISTILLATION

FIELD OF THE INVENTION

This invention relates to a method for separating acetic acid from dioxane using certain higher boiling liquids as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler.

Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Acetic acid, B.P.=118.5° C., and dioxane, B.P.=101.4° C. form a maximum azeotrope boiling at 119.5° C. and containing 77 wt.% acetic acid. When these two are found together in mixtures, either alone or with other liquids, distillation will only produce the azeotrope, never pure acetic acid or dioxane. Thus any liquid mixture containing these two will on distillation produce the azeotrope. Extractive distillation would be an attractive method of effecting the separation of acetic acid from dioxane if agents can be found that (1) will break the acetic acid—dioxane azeotrope and (2) are easy to recover from the acetic acid, that is, form no azeotrope with acetic acid and boil sufficiently above acetic acid to make the separation by rectification possible with only a few theoretical plates.

Extractive distillation typically requires the addition of an equal amount to twice as much extractive agent as the acetic acid—dioxane on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with acetic acid otherwise it will form a two-phase azeotrope with the acetic acid in the recovery column and some other method of separation will have to be employed.

OBJECTIVE OF THE INVENTION

The object of this invention is to provide a process or method of extractive distillation that will enhance the relative volatility of dioxane to acetic acid in their separation in a rectification column.

It is a further object of this invention to identify suitable extractive distillation agents which will eliminate the dioxane—acetic acid azeotrope and make possible the production of pure dioxane and acetic acid by rectification. It is a further object of this invention to identify organic compounds which are stable, can be separated from acetic acid by rectification with relatively few plates and can be recycled to the extractive distillation column and reused with little decomposition.

SUMMARY OF THE INVENTION

The objects of the invention are provided by a process for separating dioxane from acetic acid which entails the use of certain dimethylamides admixed with higher boiling organic compounds as the agent in extractive distillation.

DETAILED DESCRIPTION OF THE INVENTION

We have discovered that dimethylformamide and N,N-dimethylacetamide, either alone or admixed with other high boiling organic compounds, will effectively negate and dioxane—acetic acid maximum azeotrope and permit the separation of dioxane from acetic acid by rectification when employed as the agent in extractive distillation. Table 1 lists dimethylformamide (DMFA) and its mixtures and the approximate proportions that we have found to be effective. Table 2 lists N,N-dimethylacetamide (DMAA) and its mixtures. The data in Tables 1 and 2 was obtained in a vapor-liquid equilibrium still.

TABLE 1

Extractive Distillation Agents Containing Dimethylformamide Which Are Effective in Breaking the Acetic Acid - Dioxane Azeotrope

| Compounds | Ratios | | Relative Volatility | |
|---|---|---|---|---|
| Dimethylformamide (DMFA), Adipic acid | $(1/2)^2$ | $(3/5)^2$ | 1.9 | 1.6 |
| DMFA, Acetyl salicylic acid | " | " | 1.7 | 1.2 |
| DMFA, Azelaic acid | " | " | 2.7 | 2.3 |
| DMFA, Benzoic acid | " | " | 2.6 | 2.1 |
| DMFA, p-tert-Butyl benzoic acid | " | " | 2.0 | 1.9 |
| DMFA, Cinnamic acid | " | " | 1.8 | 2.4 |
| DMFA, Decanoic acid | " | " | 1.7 | 1.9 |
| DMFA, Glutaric acid | " | " | 3.0 | 1.7 |
| DMFA, Heptanoic acid | " | " | 2.7 | 2.3 |
| DMFA, Hexanoic acid | " | " | 1.2 | 2.2 |
| DMFA, p-Hydroxybenzoic acid | " | " | 2.0 | 3.1 |
| DMFA, Itaconic acid | " | " | 2.1 | 2.3 |
| DMFA, Neodecanoic acid | " | " | 2.0 | 2.0 |
| DMFA, Octanoic acid | " | " | 2.5 | 2.7 |
| DMFA, Pelargonic acid | " | " | 2.4 | 1.8 |

TABLE 1-continued

Extractive Distillation Agents Containing Dimethylformamide Which Are Effective in Breaking the Acetic Acid - Dioxane Azeotrope

| Compounds | Ratios | | Relative Volatility | |
|---|---|---|---|---|
| DMFA, Salicylic acid | " | " | 1.6 | 2.1 |
| DMFA, Sebacic acid | " | " | 2.1 | 2.1 |
| DMFA, o-Toluic acid | " | " | 2.0 | 1.8 |
| DMFA, m-Toluic acid | " | " | 2.3 | 2.4 |
| DMFA, p-Toluic acid | " | " | 2.2 | 1.9 |
| DMFA, Adipic acid, Ethylene glycol diacetate | $(1/3)^3$ | $(2/5)^3$ | 1.1 | 1.8 |
| DMFA, Acetyl salicylic acid, Diethylene glycol dibenzoate | " | " | 1.6 | 1.5 |
| DMFA, Azelaic acid, Benzyl ether | " | " | 1.9 | 1.7 |
| DMFA, Benzoic acid, Methyl salicylate | " | " | 2.2 | 1.7 |
| DMFA, p-tert-Butyl benzoic acid, Isobornyl acetate | " | " | 1.3 | 1.4 |
| DMFA, Cinnamic acid, Anisole | " | " | 1.4 | 2.4 |
| DMFA, Decanoic acid, Acetophenone | " | " | 2.8 | 2.0 |
| DMFA, Glutaric acid, Glycerol triacetate | " | " | 2.5 | 1.7 |
| DMFA, Heptanoic acid, Ethyl benzoate | " | " | 1.3 | 2.1 |
| DMFA, Hexanoic acid, Methyl benzoate | " | " | 2.0 | 2.2 |
| DMFA, p-Hydroxybenzoic acid, Methyl phenyl acetate | " | " | 2.1 | 2.0 |
| DMFA, Itaconic acid, Butyl ether | " | " | 1.6 | 2.2 |
| DMFA, Neodecanoic acid, Adiponitrile | " | " | 1.4 | 1.8 |
| DMFA, Octanoic acid, Benzyl benzoate | " | " | 1.7 | 1.8 |
| DMFA, Pelargonic acid, Butyl benzoate | " | " | 2.0 | 2.1 |
| DMFA, Salicylic acid, Dipropylene glycol dibenzoate | " | " | 1.3 | 1.8 |
| DMFA, Sebacic acid, Diethylene glycol diethyl ether | " | " | 2.7 | 2.0 |
| DMFA, o-Toluic acid, Diethylene glycol dimethyl ether | " | " | 2.4 | 2.6 |
| DMFA, m-Toluic acid, Benzonitrile | " | " | 2.2 | 1.9 |
| DMFA, p-Toluic acid, Ethylene glycol methyl ether acetate | " | " | 2.3 | 2.2 |

TABLE 2

Extractive Distillation Agents Containing N,N—Dimethylacetamide Which Are Effective in Breaking the Acetic Acid - Dioxane Azeotrope.

| Compounds | Ratios | | Relative Volatility | |
|---|---|---|---|---|
| N,N—Dimethylacetamide (DMAA) | 1 | 6/5 | 3.7 | 1.6 |
| DMAA, Adipic acid | $(1/2)^2$ | $(3/5)^2$ | 1.6 | 2.2 |
| DMAA, Acetyl salicylic acid | " | " | 1.6 | 2.3 |
| DMAA, Azelaic acid | " | " | 1.3 | 1.9 |
| DMAA, Benzoic acid | " | " | 2.2 | 2.2 |
| DMAA, p-tert.-Butylbenzoic acid | " | " | 1.8 | 2.4 |
| DMAA, Cinnamic acid | " | " | 2.0 | 2.2 |
| DMAA, Decanoic acid | " | " | 1.5 | 3.3 |
| DMAA, Glutaric acid | " | " | 2.7 | 1.8 |
| DMAA, Heptanoic acid | " | " | 2.0 | 2.4 |
| DMAA, Hexanoic acid | " | " | 2.3 | 3.4 |
| DMAA, 4-Hydroxybenzoic acid | " | " | 1.7 | 1.9 |
| DMAA, Malic Acid | " | " | 1.6 | 1.7 |
| DMAA, Neodecanoic acid | " | " | 1.1 | 1.7 |
| DMAA, Octanoic acid | " | " | 2.8 | 3.1 |
| DMAA, Pelargonic acid | " | " | 2.0 | 2.4 |
| DMAA, Salicylic acid | " | " | 1.8 | 1.9 |
| DMAA, Sebacic acid | " | " | 1.8 | 1.9 |
| DMAA, o-Toluic acid | " | " | 2.1 | 1.8 |
| DMAA, m-Toluic acid | " | " | 2.6 | 2.5 |
| DMAA, p-Toluic acid | " | " | 1.1 | 1.1 |
| DMAA, Adipic acid, Anisole | $(1/3)^3$ | $(2/5)^3$ | 1.6 | 1.5 |
| DMAA, Acetyl salicylic acid, Diethylene glycol diethyl ether | " | " | 3.0 | 2.1 |
| DMAA, Azelaic acid, Acetophenone | " | " | 1.8 | 1.7 |
| DMAA, Benzoic acid, Methyl phenyl acetate | " | " | 2.2 | 1.5 |
| DMAA, p-tert.-Butylbenzoic acid, Dipropylene glycol dibenzoate | " | " | 2.4 | 1.3 |
| DMAA, Cinnamic acid, Glyceryl triacetate | " | " | 2.0 | 2.1 |
| DMAA, Decanoic acid, Benzyl benzoate | " | " | 1.5 | 2.1 |
| DMAA, Glutaric acid, Isobornyl acetate | " | " | 2.0 | 2.2 |
| DMAA, Heptanoic acid, Diethylene glycol diethyl ether | " | " | 3.0 | 2.8 |
| DMAA, Heptanoic acid, Ethyl benzoate | " | " | 1.7 | 1.8 |
| DMAA, Hexanoic acid, Methyl benzoate | " | " | 1.8 | 2.3 |
| DMAA, 4-Hydroxybenzoic acid, Diethylene glycol dibenzoate | " | " | 1.5 | 1.6 |
| DMAA, Malic acid, Cyclohexanone | " | " | 1.4 | 1.2 |
| DMAA, Neodecanoic acid, Methyl salicylate | " | " | 2.1 | 2.5 |
| DMAA, Octanoic acid, Butyl benzoate | " | " | 2.4 | 2.1 |
| DMAA, Pelargonic acid, Benzyl ether | " | " | 1.4 | 2.2 |
| DMAA, Salicylic acid, Ethylene glycol diacetate | " | " | 1.4 | 1.6 |
| DMAA, Sebacic acid, Isophorone | " | " | 1.9 | 1.3 |
| DMAA, o-Toluic acid, Diethylene glycol dimethyl ether | " | " | 2.6 | 2.0 |
| DMAA, m-Toluic acid, Benzonitrile | " | " | 2.1 | 1.4 |
| DMAA, p-Toluic acid, Adiponitrile | " | " | 1.9 | 2.5 |

TABLE 3

Data From Runs Made In Rectification Column

| Agent | Column | Time hrs. | Weight % Dioxane | Weight % Acetic Acid | Relative Volatility |
|---|---|---|---|---|---|
| 50% DMFA, 50% Heptanoic acid, | Overhead | ½ | 93.5 | 6.5 | |
| | Bottoms | | 12.5 | 87.5 | 2.8 |
| | Overhead | 1 | 94 | 6 | |
| | Bottoms | | 19 | 81 | 2.5 |
| | Overhead | 1.5 | 90.6 | 9.4 | |
| | Bottoms | | 10.7 | 89.3 | 2.5 |
| 33% DMAA, 33% Heptanoic acid, 33% Diethlene glycol diethyl ether | Overhead | ½ | 67.2 | 32.8 | |
| | Bottoms | | 18.9 | 81.1 | 1.62 |
| | Overhead | 1 | 95.5 | 4.5 | |
| | Bottoms | | 16.5 | 83.5 | 3.06 |
| | Overhead | 1.5 | 94.5 | 5.5 | |
| | Bottoms | | 14.3 | 85.7 | 2.8 |

In each case, the starting material was the dioxane—acetic acid azeotrope. The ratios are the parts by weight of extractive agent used per part of dioxane—acetic acid azeotrope.

The relative volatilities are listed for each of the two ratios employed. The compounds which are effective when used with DMFA are adipic acid, acetyl salicylic acid, azelaic acid, benzoic acid, p-tertiary butyl benzoic acid, cinnamic acid, decanoic acid, glutaric acid, heptanoic acid, hexanoic acid, p-hydroxybenzoic acid, itaconic acid, neodecanoic acid, octanoic acid, pelargonic acid, salicylic acid, sebacic acid, o-toluic acid, m-toluic acid, p-toluic acid, ethylene glycol diacetate, diethylene glycol dibenzoate, benzyl ether, methyl salicylate, isobornyl acetate, anisole, acetophenone, glycerol triacetate, ethyl benzoate, methyl benzoate, methyl phenyl acetate, butyl ether, adiponitrile, benzyl benzoate, butyl benzoate, dipropylene glycol dibenzoate, diethylene glycol diethyl ether, diethylene glycol dimethyl ether, benzonitrile and ethylene glycol methyl ether acetate.

The same compounds are also effective with N,N-dimethylacetamide (DMAA).

The two relative volatilities shown in Tables 1 and 2 correspond to the two different ratios employed. For example, in Table 2, one part of DMAA mixed with one part of the dioxane—acetic acid azeotrope gives a relative volatility of 3.7; with 6/5 parts of DMAA, the relative volatility is 1.6. One half part of DMAA mixed with one half part of adipic acid with one part of dioxane—acetic acid azeotrope gives a relative volatility of 1.6; 3/5 parts of DMAA plus 3/5 parts of adipic acid give 2.2. One third part of DMAA plus ⅓ part of cinnamic acid plus ⅓ part of glycerol triacetate mixed with one part of the dioxane—acetic acid azeotrope gives a relative volatility of 2.0; with 2/5 parts, these three give a relative volatility of 2.1. In every example in Tables 1 and 2, the starting material is the dioxane—acetic acid azeotrope which possesses a relative volatility of 1.00.

Two of the mixtures listed in Tables 1 and 2 and whose relative volatility had been determined in the vapor-liquid equilibrium still, were then evaluated in a glass perforated plate rectification column possessing 4.5 theoretical plates and the results listed in Table 3.

The data in Table 3 was obtained in the following manner. The charge was 250 grams of the dioxane—acetic acid azeotrope and after a half hour of operation in the 4.5 theoretical plate column to establish equilibrium, 50% DMFA and 50% heptanoic acid at 95° C. and 20 ml/min. was pumped in. The rectification was continued with sampling of the overhead and bottoms after ½ hour, one hour and 1.5 hours. The analyses are shown in Table 3 and were 90.6% dioxane, 9.4% acetic acid in the overhead and 10.7% dioxane, 89.3% acetic acid in the bottoms which gives a relative volatility of 2.5 of dioxane to acetic acid. This indicates that the maximum azeotrope has been negated and separation accomplished. Without the extractive agent, the overhead would have been the maximum azeotrope composition of 23% dioxane.

This proves that the extractive agent is negating the azeotrope and makes the rectification proceed as if the azeotrope no longer existed and brings out the more volatile dioxane, as overhead.

THE USEFULNESS OF THE INVENTION

The usefulness or utility of this invention can be demonstrated by referring to the data presented in Tables 1, 2 and 3. All of the successful extractive distillation agents show that dioxane and acetic acid can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity dioxane and acetic acid from any mixture of these two including the maximum azeotrope. The stability of the compounds used and the boiling point difference is such that complete recovery and recycle is obtainable by a simple distillation and the amount required for make-up is small.

WORKING EXAMPLES

Example 1

Fifty grams of the dioxane—acetic acid azeotrope and 50 grams of N,N-dimethylacetamide (DMAA) were charged to a vapor-liquid equilibrium still and refluxed for 16 hours. Analysis indicated a vapor composition of 34% dioxane, 66% acetic acid, a liquid composition of 13.8% dioxane, 86.2% acetic acid which is a relative volatility of 3.7. Ten grams of DMAA were added and refluxing continued for another two hours. Analysis indicated a vapor composition of 21% dioxane, 79% acetic acid, a liquid composition of 14.4% dioxane, 85.6% acetic acid which is a relative volatility of 1.6.

Example 2

Fifty grams of the dioxane—acetic acid azeotrope, 25 grams of DMAA and 25 grams of adipic acid were charged to the vapor-liquid equilibrium still and refluxed for 15 hours. Analysis indicated a vapor composition of 23.2% dioxane,, 76.8% acetic acid and a liquid composition of 16.1% dioxane, 83.9% acetic acid which is a relative volatility of 1.6. Five grams of DMAA and five grams of adipic acid were added and refluxing continued for another eight hours. Analysis indicated a vapor composition of 22.2% dioxane, 77.8% acetic acid and a liquid composition of 11.2% dioxane, 88.8% acetic acid which is a relative volatility of 2.2.

Example 3

Fifty grams of the dioxane—acetic acid azeotrope, 17 grams of DMAA, 17 grams of cinnamic acid and 17 grams of glycerol triacetate were charged to the vapor-liquid equilibrium still and refluxed for ten hours. Analysis indicated a vapor composition of 26.3% dioxane, 73.7% acetic acid and a liquid composition of 13.5% dioxane, 86.5% acetic acid which is a relative volatility of 2.0. Three grams each of DMAA, cinnamic acid and glycerol triacetate were added and refluxing continued for another three hours. Analysis indicated a vapor composition of 23.9% dioxane, 76.1% acetic acid and a liquid composition of 12.8% dioxane, 87.2% acetic acid which is a relative volatility of 2.1.

Example 4

A glass perforated plate rectification column was calibrated with ethylbenzene and p-xylene which possesses a relative volatility of 1.06 and found to have 4.5 theoretical plates. A solution comprising 250 grams of the dioxane—acetic acid azeotrope was placed in the stillpot and heated. When refluxing began, an extractive agent comprising 50% DMFA, 50% heptanoic acid was pumped into the column at a rate of 20 ml/min. The temperature of the extractive agent as it entered the column was 95° C. After establishing the feed rate of the extractive agent, the heat input to the dioxane and acetic acid in the stillpot was adjusted to give a total reflux rate of 10-20 ml/min. After 1.5 hours of operation, the overhead and bottoms samples of approximately two ml. were collected and analysed by gas chromatography.

The overhead analysis was 90.6% dioxane, 9.4% acetic acid. The bottoms analysis was 10.7% dioxane, 89.3% acetic acid. Using these compositions in the Fenske equation, with the number of theoretical plates in the column being 4.5, gave an average relative volatility of 2.5 for each theoretical plate.

Example 5

Using the same procedure as in Example 4, a feed comprising 33% DMAA, 33% heptanoic acid and 33% diethylene glycol diethyl ether was pumped into the column at 95° C. and 20 ml/min. After 1.5 hours of operation, the overhead analysis was 94.5% dioxane, 5.5% acetic acid and a bottoms analysis of 14.3% dioxane, 85.7% acetic acid which is a relative volatility of 2.8.

We claim:

1. A method for recovering dioxane from mixtures of dioxane and acetic acid which comprises distilling a mixture of dioxane and acetic acid in a rectification column in the presence of about one part of an extractive agent per part of dioxane—acetic acid mixture, recovering dioxane as overhead product and obtaining the acetic acid and the extractive agent from the stillpot, wherein said extractive agent comprises N,N-dimethylacetamide.

2. The method of claim 1 in which the extractive agent comprises N,N-dimethylacetamide and at least one member from the group consisting of adipic acid, acetyl salicylic acid, azelaic acid, benzoic acid, p-tertiary butyl benzoic acid, cinnamic acid, decanoic acid, glutaric acid, heptanoic acid, hexanoic acid, 4-hydroxybenzoic acid, malic acid, neodecanoic acid, octanoic acid, pelargonic acid, salicylic acid, sebacic acid, o-toluic acid, m-toluic acid, p-toluic acid, anisole, diethylene glycol diethyl ether, acetophenone, methyl phenyl acetate, dipropylene glycol dibenzoate, glycerol triacetate, benzyl benzoate, isobornyl acetate, ethyl benzoate, methyl benzoate, cyclohexanone, diethylene glycol dibenzoate, methyl salicylate, butyl benzoate, benzyl ether, ethylene glycol diacetate, isophorone, benzonitrile, diethylene glycol dimethyl ether and adiponitrile.

3. A method for recovering dioxane from mixtures of dioxane and acetic acid which comprises distilling a mixture of dioxane and acetic acid in a rectification column in the presence of about one part of an extractive agent per part of dioxane—acetic acid mixture, recovering dioxane as overhead product and obtaining the acetic acid and the extractive agent from the stillpot, wherein said extractive agent comprises dimethylformamide and at least one member from the group consisting of adipic acid, acetyl salicylic acid, azelaic acid, benzoic acid, p-tertiary butyl benzoic acid, cinnamic acid, decanoic acid, glutaric acid, heptanoic acid, hexanoic acid, p-hydroxybenzoic acid, itaconic acid, neodecanoic acid, octanoic acid, pelargonic acid, salicylic acid, sebacic acid, o-toluic acid, m-toluic acid, p-toluic acid, ethylene glycol diacetate, diethylene glycol dibenzoate, benzyl ether, methyl salicylate, isobornyl acetate, anisole, acetophenone, glycerol triacetate, ethyl benzoate, methyl benzoate, butyl ether, methyl phenyl acetate, adiponitrile, benzyl benzoate, butyl benzoate, dipropylene glycol dibenzoate, diethylene glycol diethyl ether, diethylene glycol dimethyl ether, benzonitrile and ethylene glycol methyl ether acetate.

* * * * *